US00PP21243P2

(12) United States Plant Patent
Kleinhanns

(10) Patent No.: US PP21,243 P2
(45) Date of Patent: Aug. 24, 2010

(54) ***SALVIA* PLANT NAMED 'FLORSALWHITE'**

(50) Latin Name: ***Salvia nemorosa* L.**
Varietal Denomination: Florsalwhite

(75) Inventor: Christoph E. Kleinhanns, Gernrode (DE)

(73) Assignee: Florensis Hamer CS, Hendrik Ido Ambacht (NL)

( * ) Notice: Subject to any disclaimer, the term of this patent is extended or adjusted under 35 U.S.C. 154(b) by 0 days.

(21) Appl. No.: 12/378,269

(22) Filed: Feb. 10, 2009

(51) Int. Cl.
*A01H 5/00* (2006.01)

(52) U.S. Cl. ..... Plt./475

(58) Field of Classification Search ..... Plt./475
See application file for complete search history.

*Primary Examiner*—Wendy C Haas
(74) *Attorney, Agent, or Firm*—Jondle & Associates, P.C.

(57) ABSTRACT

A new *Salvia* plant particularly distinguished by its white flower color, excellent branching habit, multiple flowers and increased resistance to fungal disease is disclosed.

2 Drawing Sheets

Genus and species: *Salvia nemorosa* L.
Variety denomination: 'Florsalwhite'.

BACKGROUND OF THE NEW PLANT

The present invention comprises a new and distinct cultivar of *Salvia*, botanically known as *Salvia nemorosa* L. and hereinafter referred to by the cultivar name 'Florsalwhite'. The new cultivar originated from an uncontrolled cross made in June 2003 in Quedlinburg, Sachsen-Anhalt, Germany. The female parent was a proprietary *Salvia* plant named '2398-12' (unpatented) with white to light-rose flowers. The male parent was an unknown *Salvia* plant.

The new cultivar was first propagated in March 2006 in H.I. Ambacht, The Netherlands, and has been asexually reproduced over three generations over a two-year period. The present invention has been found to retain its distinctive characteristics through successive asexual propagations.

Plant Breeder's Rights for this cultivar have not been applied for. 'Florsalwhite' has not been made publicly available more than one year prior to the filing of this application.

SUMMARY OF THE INVENTION

The following are the most outstanding and distinguishing characteristics of this new cultivar when grown under normal horticultural practices in Quedlinburg, Sachsen-Anhalt, Germany.

1. Pure white flower color;
2. Good branching habit;
3. Many flowers; and
4. High tolerance to fungal diseases

DESCRIPTION OF PHOTOGRAPHS

This new *Salvia* plant is illustrated by the accompanying photographs which show overall plant habit including blooms, buds, and foliage of the plant; the colors shown are as true as can be reasonably obtained by conventional photographic procedures. The photographs are of a plant about 4 months old, grown in a greenhouse in Quedlinburg, Sachsen-Anhalt, Germany, in the spring of 2008.

DESCRIPTION OF THE NEW CULTIVAR

Figure 1:
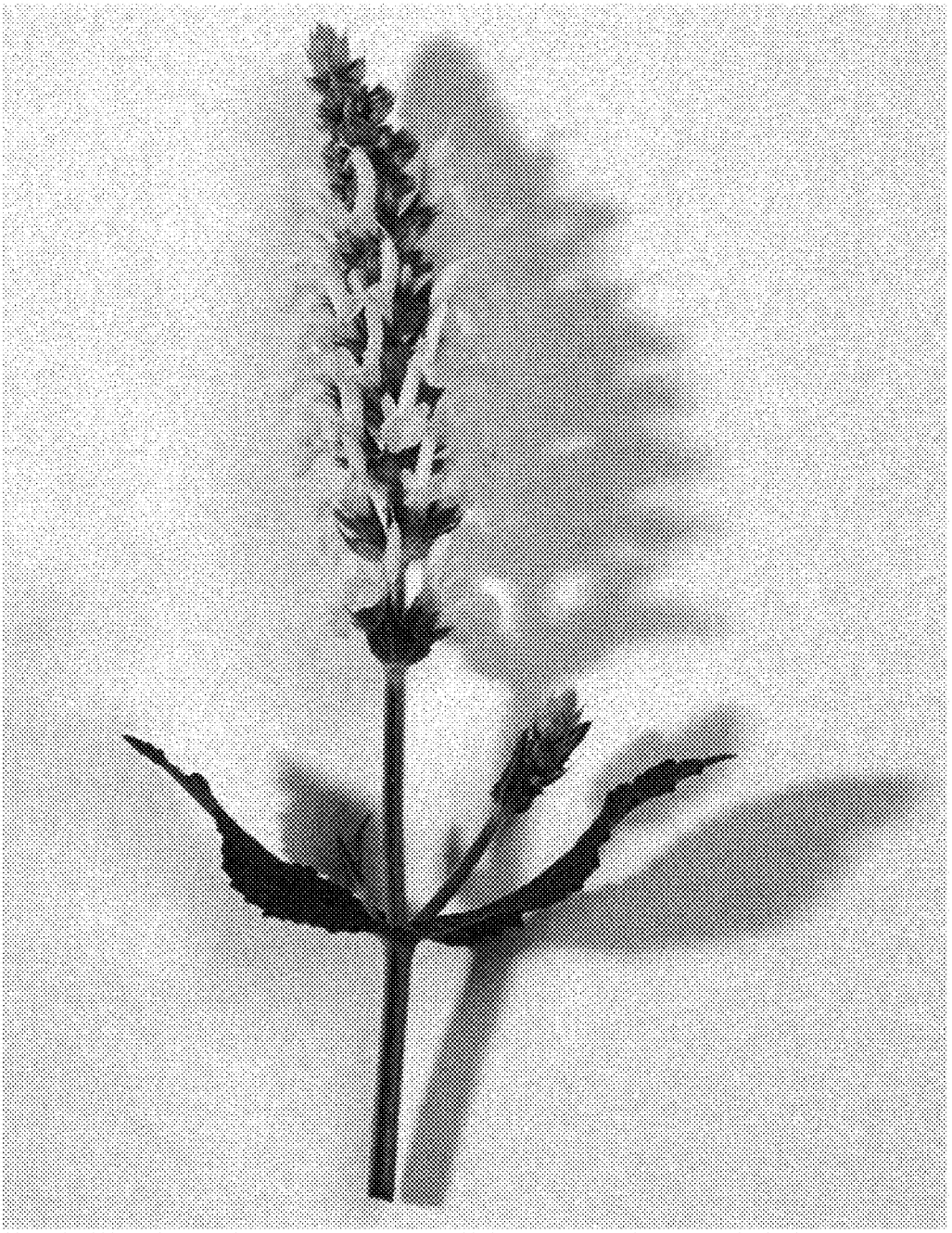
FIG. 1 shows a close-up of the mature flowers.
Figure 2:
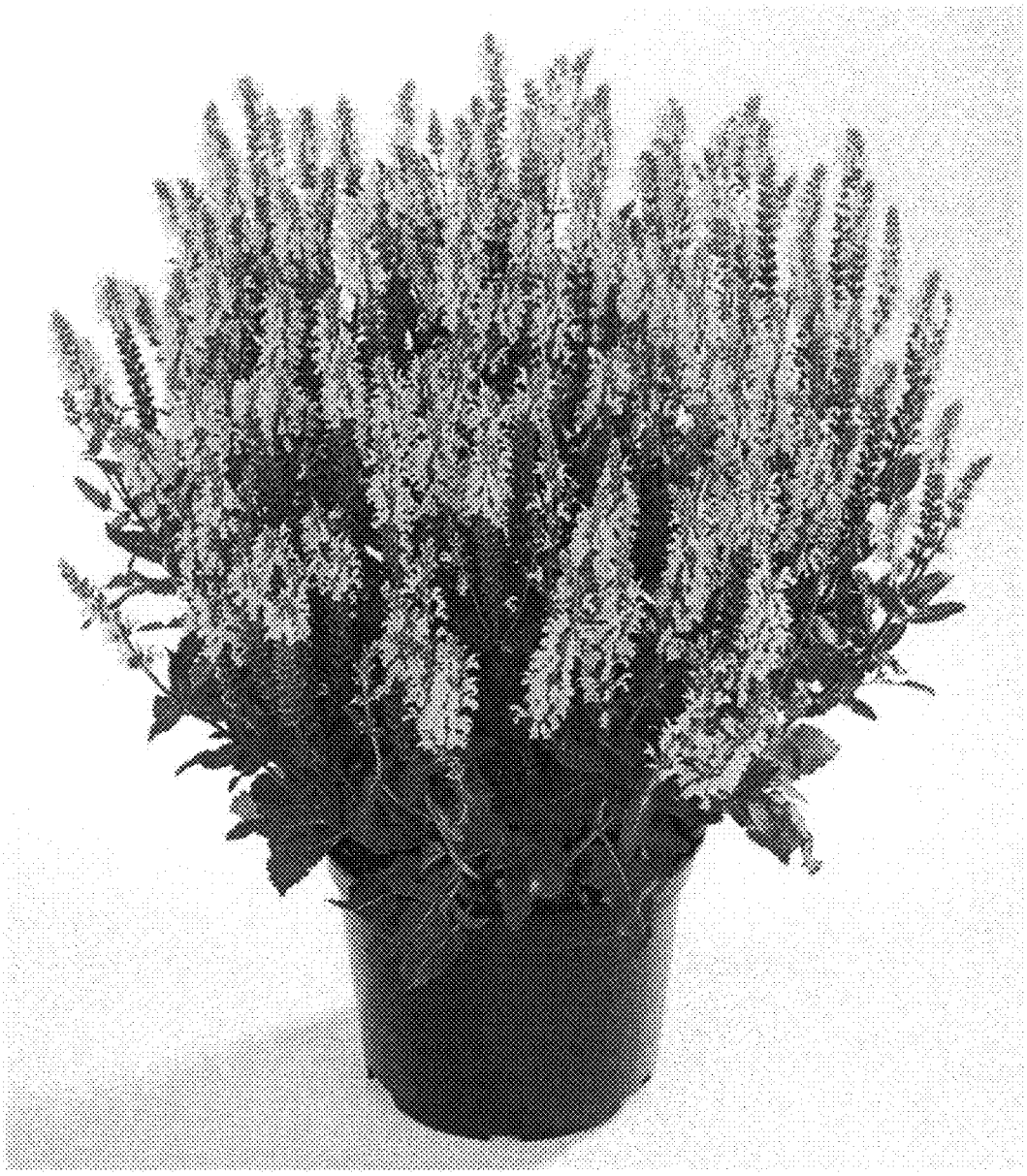
FIG. 2 shows the overall plant habit, including blooms, buds, and foliage.

The following detailed description sets forth the distinctive characteristics of 'Florsalwhite'. The data which defines these characteristics were collected from asexual reproductions carried out in Quedlinburg, Sachsen-Anhalt, Germany. The plant history was taken on 4 month old plants which were grown in a greenhouse. Color readings were taken under natural light in the greenhouse. Color references are primarily to The R.H.S. Colour Chart of The Royal Horticultural Society of London (R.H.S.) (1986).

DETAILED BOTANICAL DESCRIPTION OF THE NEW PLANT

Classification:
- *Botanical name.*—*Salvia nemorosa* L.
- *Common name.*—Woodland Sage.

Parentage:
- *Female parent.*—Proprietary *Salvia* plant named '2398-12' (unpatented).
- *Male parent.*—Unknown *Salvia* plant.

Plant:
- *Form and habit.*—Spreading, upright.
- *Height (from top of soil).*—25.0 cm.
- *Width (including flowers).*—30.0 cm.
- *Outdoor plant performance.*—Spring through autumn.

Leaves:
- *Arrangement.*—Opposite.
- *Shape.*—Lanceolate.
- *Apex.*—Acute.
- *Base.*—Subcordate.
- *Margin.*—Crenulate.
- *Immature.*—Length: 2.0 cm to 3.0 cm. Width: 1.5 cm.
- *Mature (fully expanded).*—Length: 7.0 cm. Width: 2.7 cm.
- *Color, immature (upper and lower surface).*—RHS 137A to RHS 137B.

*Color, mature* (*upper and lower surface*).—RHS 137A to RHS 137B.
*Venation, immature.*—Type: Reticulate. Color: RHS 145D.
*Venation, mature.*—Type: Reticulate. Color: RHS 145D.
*Texture.*—Upper surface: Smooth. Lower surface: Pubescent.
*Petiole.*—Length: 1.2 cm. Diameter: 0.2 cm. Texture (both surfaces): Pubescent.
*Pubescence color* (*both surfaces*).—RHS 150D (Transparent).

Stem:
*Length* (*excluding inflorescence*).—10.0 cm to 15.0 cm.
*Diameter.*—0.3 cm to 0.4 cm.
*Internode length.*—2.0 cm to 4.0 cm.
*Texture.*—Pubescent.
*Color.*—RHS 137C.

Flower:
*Arrangement.*—In verticillasters on spikes.
*Shape.*—Spike.
*Flowering season.*—Spring to autumn.
*Flower buds.*—Length: 0.4 cm. Diameter: 0.2 cm. Shape: Round. Color: White.
*Inflorescence.*—Length: 10.0 cm to 12.0 cm. Diameter: 1.5 cm. Quantity of inflorescences per plant: 20 to 40.
*Flowers.*—Diameter: 0.2 cm. Depth/height: 0.8 cm.
*Lastingness of individual blooms on the plant.*—1 to 2 days.
*Fragrance.*—Absent.

Petals:
*Arrangement.*—One upper lip and one lower lip with two lobes; lips fused at the base.
*Length.*—Upper petal: 0.5 cm. Lower petal: 0.3 cm.
*Width* (*upper and lower petal*).—0.2 cm.
*Shape* (*upper and lower petal*).—Labiate.
*Apex.*—Upper petal: Obtuse. Lower petal: Rounded.
*Texture* (*upper and lower petal*).—Slightly pubescent.
*Color* (*when opening*).—Upper petal (both surfaces): RHS 155 (White). Lower petal (both surfaces): RHS 155 (White).
*Color* (*fully open*).—Upper petal (both surfaces): RHS 155 (White). Lower petal (both surfaces): RHS 155 (White).

Sepals:
*Arrangement.*—2 sepals fused to form a tube.
*Length.*—0.4 cm.
*Width.*—0.25 cm.
*Shape.*—Apiculate.
*Apex.*—Apiculate.
*Base.*—Rounded.
*Margin.*—Smooth.
*Texture* (*both surfaces*).—Smooth.
*Color* (*immature*) (*both surfaces*).—RHS 141D.
*Color* (*mature*) (*both surfaces*).—RHS 141D.
*Longitudinal stripes color* (*immature*) (*both surfaces*).—RHS 141B.
*Longitudinal stripes color* (*mature*) (*both surfaces*).—RHS 141B.

Penduncle:
*Color.*—RHS 150D (Transparent).
*Length.*—0.1 cm.
*Diameter.*—0.05 cm.
*Aspect.*—45°.
*Texture.*—Smooth.

Reproductive organs:
*Stamens.*—Quantity per flower: 2. Filament length: 0.1 cm. Filament color: Transparent white.
*Anther.*—Anther color: RHS 161C. Length: 0.1 cm.
*Pollen color.*—RHS 161D.
*Pollen amount.*—Moderate.
*Pistil.*—Pistil length: 0.8 cm to 1.0 cm. Pistil quantity: 1.
*Stigma.*—Color: Transparent white. Shape: Forked.
*Style.*—Length: 0.8 cm to 1.0 cm. Color: Transparent white.
*Ovary color.*—RHS 141D.

Fruit and seed set: Maximum of 4 oval seeds per flower; often not germinating.

Seed:
*Shape.*—Oval to round.
*Length.*—0.15 cm to 0.16 cm.
*Width.*—0.11 cm to 0.15 cm.
*Color.*—Matte black with white marks.

Disease and insect resistance: Resistance is typical of the species, but with a high tolerance for fungal diseases.

COMPARISON WITH PARENTAL AND COMMERCIAL CULTIVARS

'Florsalwhite' differs from the female parent '2398-12' (unpatented) by having pure white flowers with an excellent branching habit while '2398-12' has white to light rose flowers and less branching habit.

'Florsalwhite' differs from the commercial cultivar 'Schneehügel' (unpatented) by having an excellent branching habit with multiple flowers while 'Schneehügel' has a habit with less branching and flowers.

I claim:

1. A new and distinct cultivar of *Salvia* plant as shown and described herein.

* * * * *